United States Patent [19]
Mandai et al.

[11] Patent Number: 5,780,620
[45] Date of Patent: Jul. 14, 1998

[54] NON-REDUCING OLIGOSACCHARIDES AND THEIR PRODUCTION AND USE

[75] Inventors: Takahiko Mandai; Takashi Shibuya; Toshiyuki Sugimoto; Toshio Miyake, all of Okayama, Japan

[73] Assignee: Kabushiki Kaisha Hayashibara Seibutsu Kagaku Kenkyujo, Okayama, Japan

[21] Appl. No.: 762,940

[22] Filed: Dec. 10, 1996

Related U.S. Application Data

[63] Continuation of Ser. No. 267,134, Jun. 28, 1994, abandoned.

[30] Foreign Application Priority Data

Jun. 28, 1993 [JP] Japan .................................. 5-178623
Mar. 1, 1994 [JP] Japan .................................. 6-054377

[51] Int. Cl.$^6$ .................. C07H 1/00; C12P 19/14; A61K 31/715
[52] U.S. Cl. .................. 536/123.1; 536/102; 536/103; 536/123.12; 536/124; 514/54; 514/58; 514/60; 435/95; 435/96; 435/97; 435/98; 435/101
[58] Field of Search .................. 536/102, 103, 536/123.1, 123.12, 124; 514/54, 58, 60; 435/95, 96, 97, 98, 101

[56] References Cited

U.S. PATENT DOCUMENTS

| | | | |
|---|---|---|---|
| 3,819,484 | 6/1974 | Okada et al. | 435/97 |
| 4,359,458 | 11/1982 | Nair et al. | 514/54 |
| 4,762,917 | 8/1988 | Ikenaka et al. | 536/4.1 |
| 5,141,858 | 8/1992 | Paul et al. | 435/97 |
| 5,298,616 | 3/1994 | Hosang et al. | 536/118 |
| 5,319,076 | 6/1994 | Hasegawa et al. | 536/4.1 |
| 5,378,831 | 1/1995 | Usui et al. | 536/123.1 |
| 5,393,660 | 2/1995 | Kitahata et al. | 435/22 |
| 5,455,168 | 10/1995 | Maruta et al. | 435/201 |

FOREIGN PATENT DOCUMENTS

| | | |
|---|---|---|
| 2055257 | 3/1993 | Canada . |
| 0289138 | 3/1987 | European Pat. Off. . |
| 0479093 | 4/1992 | European Pat. Off. . |
| 5823799 | 8/1981 | Japan . |
| 59-148794 | 2/1983 | Japan . |
| 2106912 | 8/1982 | United Kingdom . |
| 9203565 | 3/1992 | WIPO . |

OTHER PUBLICATIONS

*Catalogue of Strains*; The American Type Culture Collection; Tenth Edition; 1972.
*Catalogue of Bacteria & Bacteriophages*; The American Type Culture Collection; 18th Edition; 1992.
Tipson et al; *Carbon–13 Nuclear Magnetic Resonance Data for Oligosaccharides*; Advances in Carbohydrate Chemistry and Biochemistry; vol. 42; 1984.
Stodola et al; *The Preparation, Properties and Structure of the Diasaccharide Leucrose*; Journal of American Chemical Society; vol. 78; Jun. 5, 1956.
*List of Cultures*; Institute for Fermentation; Eight Edition; vol. 1; 1988.
*List of Cultures*; Institute for Fermentation; Nineth Edition; 1992.
*List of Cultures*; Institute for Fermentation; Third Edition; 1962.
*List of Cultures*; Institute for Fermentation; Seventh Edition; 1984.
Wessel et al. *Helv. Chim. Acta* 1991, 74, 682–696.
Shibuya et al. *Biosci. Biotech. Biochem.* 1993, 57(1), 56–60.
Kadkhodaei et al. *Biopolymers* 1991, 31(13), 1581–92.
MacGregor et al. *Carbohydr. Res.* 1994, 257(2), 249–268.

Primary Examiner—Kathleen K. Fonda
Attorney, Agent, or Firm—Browdy and Neimark

[57] ABSTRACT

Novel non-reducing oligosaccharide having a structure represented by the formula of alpha-D-oligoglucosyl alpha-D-oligoglucoside is obtained by exposing either an aqueous solution which contains trehalose and an alpha-glucosyl saccharide or an aqueous solution which contains a non-reducing saccharide bearing a trehalose structure at its end to a saccharide-transferring enzyme. The oligosaccharide has a reduced sweetness, superior stability, appropriate viscosity and less or no susceptibility to crystallization or superior solubility when in crystalline form. These features make the oligosaccharide very useful in various compositions including foods, beverages, cosmetics, pharmaceuticals and shaped bodies.

15 Claims, 6 Drawing Sheets

NON-REDUCING OLIGOSACCHARIDES AND THEIR PRODUCTION AND USE

This application is a continuation of application Ser. No. 08/267,134, filed Jun. 28, 1994, now abandoned.

BACKGROUND OF THE INVENTION

1. Field of the Invention

This invention relates to a novel saccharide and its production and use, in particular, to a non-reducing oligosaccharide represented by the general formula of alpha-D-oligoglucosyl alpha-D-oligoglucoside, as well as to its production and use.

2. Description of the Prior Art

There have been known several distinct types of non-reducing oligosaccharides: a type where as found in sucrose, erlose, raffinose, melezitose and kestose, glucose and fructose are bound via the alpha-1 and beta-2 linkages, in other words, oligosaccharides having a sucrose structure in the molecules; sugar alcohols such as maltitol, maltotriitol and lactitol; and trehalose where glucoses are bound to each other via the alpha-1 and alpha-1 linkages. Oligosaccharides which bear a sucrose structure in the molecules are however readily decomposable in acidic solutions because the sucrose structure is labile. These do restrict the processing of foods, beverages and the like. Sugar alcohols, which are usually prepared by hydrogenation at elevated pressure, have a superior stability, as well as having the demerit that when excessively ingested they may induce diarrhea because they are less digestable and assimilable in human body. Trehalose is very stable and the present inventors found that it is readily digested and assimilated into energy in human body. Also it was found that trehalose is however low in molecular weight, inferior in viscosity, too high in crystallizability therefore when used in concentrated aqueous solution form, crystals educe during the storage and these restrict uses in the food industry. Thus there has been a strong demand for the development of higher non-reducing oligosaccharides which are superior in stability, digestibility and assimilability, as well as having an appropriate viscosity, less or no susceptibility to crystallization or superior solubility when in crystalline form.

OBJECT OF THE INVENTION

This invention is to provide a novel non-reducing oligosaccharide bearing a trehalose structure in the molecule and also having either less or no susceptibility to crystallization or superior solubility when in crystalline form, as well as to provide its production and use.

SUMMARY OF THE INVENTION

To establish such a non-reducing oligosaccharide and its production, the present inventors studied various means which can bind additional saccharides to both glucosyl groups present in the trehalose molecule. This study eventually led to the finding that the objectives are attainable by exposing either an aqueous solution which contains trehalose and an alpha-glucosyl saccharide or an aqueous solution which contains a non-reducing saccharide bearing a trehalose structure at its end (such saccharide may be referred to as "alpha-D-oligoglucosyl alpha-D-oligoglucoside" in this invention), as disclosed in Japan Patent Application No. 362,131/92 by the same applicant, to the action of a saccharide-transferring enzyme, thus completing this invention. In particular, this invention establishes a novel non-

2 reducing oligosaccharide where one or several glucosyl groups are bound to both glucosyl groups in trehalose, in addition to a process to produce the same. Further this invention provides several uses of the non-reducing oligosaccharide where its characteristics including superior stability, appropriate viscosity, non or less crystallizability or superior solubility when in crystalline form, tastelessness or reduced sweetness and assimilability into energy on oral intake are utilized.

DETAILED DESCRIPTION OF THE INVENTION

Although the non-reducing oligosaccharide of this invention can be synthesized in chemical manner, it is much more favorable with industrial viewpoint to employ biochemical reactions, in particular, those wherein a saccharide-transferring enzyme is allowed to act either on an aqueous solution which contains trehalose and an alpha-glucosyl saccharide or on an aqueous solution which contains a non-reducing saccharide bearing a trehalose structure at its end. Preferable trehalose sources are syrups and powders which have the possible highest trehalose content, usually, 5 w/w % or more, desirably, 20 w/w % or more, much more desirably, powders which contain 50 w/w % or more trehalose (the percentages as used hereinafter shall mean "w/w %" unless specified otherwise). To prepare such a syrup or powder, processes where reducing partial starch hydrolysates are enzymatically converted, in particular, those disclosed in Japan Patent Applications No. 362,131/92, No. 156,338/93 and No. 199,971/93 by the same applicant are favorably feasible because they facilitate large-scale production. If necessary, commercially-available trehalose can be arbitrarily used.

The alpha-glucosyl saccharides feasible in this invention are those which bear alpha-glucoside linkages, for example, starch, gelatinized starch, liquefied starch, solubilized starch, amylose, amylopectin, reducing partial starch hydrolysate, saccharide-transferred starch product, cyclodextrin, dextrin, maltooligosaccharide and sucrose.

The non-reducing saccharides favorably usable in this invention are those which are, as disclosed in Japan Patent Application No. 362,131/92 by the same applicant, preparable by exposing reducing partial starch hydrolysates to the action of an enzyme which forms a non-reducing saccharide bearing a trehalose structure at its ends from a reducing partial starch hydrolysate with a glucose polymerization degree of 3 or higher (such enzyme may be designated as "non-reducing saccharide-producing enzyme" in this invention). As disclosed in Japan Patent Application No. 349,216/93 by the same applicant, such a non-reducing saccharide-producing enzyme may be either a culture of microorganisms which are capable of producing the enzyme, for example, Rhizobium species M-11 and Arthrobacter species Q36 which have been deposited at the Patent Microorganism Depository, National Institute of Bioscience and Human-technology, Agency of Industrial Science and Technology, 1-3, Higashi 1 chome, Tsukuba-shi, Ibaraki-ken, Japan, under the accession numbers of FERM BP-4130 and FERM BP-4316 respectively, and conventional microorganisms including *Brevibacterium helovolum* (ATCC 11822), *Flavobacterium aguatile* (IFO 3772), *Micrococcus luteus* (IFO 3064), *Micrococcus roseus* (ATCC 186), *Curtobacterium citreum* (IFO 15231), *Mycobacterium smegmatis* (ATCC 19420) and *Terrabacter tumescens* (IFO 12960), or an enzyme preparation which is obtainable by arbitrarily purifying such a culture by conventional methods. Such a culture or enzyme preparation has a property of forming non-reducing saccharides bearing a trehalose structure at their ends from one or more reducing partial starch hydrolysates with a glucose polymerization degree of 3 or higher.

In the production of such a non-reducing saccharide, it is favorable to allow the aforementioned non-reducing saccharide-producing enzyme to act on non-reducing partial starch hydrolysates which are usually prepared by exposing alpha-glucosyl saccharides, for example, reducing partial starch hydrolysates, for example, starch, gelatinized starch, liquefied starch, solubilized starch, amylose, amylopectin and dextrin, to the action of alpha-amylase or to alpha-amylase and starch-debranching enzyme.

As to the saccharide-transferring enzyme, cyclomaltodextrin glucanotransferase (EC 2.4.1.19) is the best but others, for example, alpha-amylase (EC 3.2.1.1) and alpha-glucosidase (EC 3.2.1.20) can be used, if necessary. In the case of using cyclomaltodextrin glucanotransferase, those enzymes from conventional microorganisms of the genus Bacillus or Klebsiella are arbitrarily chosen. The alpha-amylase includes those from microorganisms of the genus Bacillus, in particular, saccharifying alpha-amylases therefrom. The alpha-glucosidase includes conventional microorganisms and enzymes, for example, of the genera Penicillium and Mucor, in addition to enzymes from plants such as rice and wheat seeds.

Any saccharide-transfer reactions can be used in this invention as long as they give the non-reducing oligosaccharide of this invention, and arbitrarily chosen depending on the enzyme to be used. For example, in the case of using cyclomaltodextrin glucanotransferase or alpha-amylase, one can choose reactions which permit either enzyme to act on an aqueous solution containing trehalose and an alpha-glucosyl saccharide such as liquefied starch and reducing partial starch hydrolysate so that one or more alpha-glucosyl groups are transferred from the alpha-glucosyl saccharide to both glucosyl groups in trehalose to give the non-reducing oligosaccharide of this invention. In this case, the weight ratio of alpha-glucosyl saccharide to trehalose usually lies in the range of 0.1- to 100-folds, desirably, 0.2- to 20-folds. Alternatively, the alpha-D-oligoglucosyl alpha-D-oligoglucoside can be prepared by exposing a non-reducing saccharide bearing a trehalose structure at its to the action of cyclomatodextrin glucanotransferase. In the case of using alpha-glucosidase, for example, one can choose reactions which permit the enzyme to act on an aqueous solution containing trehalose and an alpha-glucosyl saccharide, for example, dextrin, maltooligosaccharide and sucrose having a relatively low molecular weight so that alpha-glucosyl groups are transferred from the alpha-glucosyl saccharide to both glucosyl groups in trehalose. In this case, the weight ratio of alpha-glucosyl saccharide to trehalose usually lies in the range of 0.1- to 100-folds, desirably, 0.2- to 20-folds.

These enzymatic reactions are usually carried out at a temperature of 20°–80° C. and a pH of 3–9 and the enzymes and microorganisms per se can be repeatedly used in continuous or batchwise manner when immobilized by conventional method, for example, carrier-binding method, cross-linking method and entrapping method. Among the aforementioned saccharide-transfer reactions, the reaction using cyclomaltodextrin glucanotransferase is generally most favorable with industrial viewpoint because it permits the use of cheaper alpha-glucosyl saccharides as saccharide donor and gives an elevated yield for alpha-D-oligoglucosyl alpha-D-oligoglucoside: In particular, the use of cyclomaltodextrin glucanotransferases from *Bacillus stearothermophilus* is extremely favorable because they can be used at an elevated temperature and this suppresses the retrogradation of amylaceous substances and microbial contamination in reaction mixtures, as well as speeding up the enzymatic reaction. In this case, when either an aqueous solution which contains trehalose along with an alpha-glucosyl saccharide, for example, gelatinized starch, liquefied starch, reducing partial starch hydrolysate with a DE of 1–50, amylodextrin and cyclodextrin or an aqueous solution which contains a non-reducing saccharide bearing a trehalose structure at its end is exposed to 0.1 units/g alpha-glucosyl saccharide or more, desirably, 1–25 units/g alpha-glucosyl saccharide of such a cyclomaltodextrin glucanotransferase for 1–100 hours, desirably, 4–70 hours, non-reducing oligosaccharides (as abbreviated by "Gm-T-Gn" where "G" and "T" mean glucose residue and alpha, alpha-trehalose respectively, while "m" and "n" mean integers ranging from 1–8), for example, maltosyl maltoside, maltotriosyl maltoside, maltotriosyl maltotrioside, maltotetraosyl maltotrioside, maltotetraosyl maltotetraoside, maltopentaosyl maltotetraoside and maltopentaosyl maltopentaoside where one or several alpha-glucosyl groups have been transferred to both glucosyl groups in trehalose are formed. If necessary, these can be further exposed to one or more hydrolases, in particular, beta-amylase (EC 3.2.1.2) or beta-amylase and a starch-debranching enzyme such as pullulanase and isoamylase to accumulate maltosyl maltoside, maltotriosyl maltoside and maltotriosyl maltotrioside as predominant products, followed by collecting them.

Solutions which usually contain tip to 5–60%, on dry solid basis, of a tetra or higher alpha-D-oligoglucosyl alpha-D-oligoglucoside formed by the aforementioned saccharide-transfer reaction or combination with hydrolysis can be used in liquid, syrup or solid form after filtration, purification, concentration and dehydration using spray-drying or lyophilization.

Generally to fully exert the features of lower alpha-D-oligoglucosyl alpha-D-oligoglucosides, after completion of saccharide-transfer reaction and subsequent hydrolysis, the resultant solution which contains tetra-, penta- and hexasaccharides is used intact or subjected to further separation and purification into tetra-, penta- and hexasaccharide-rich products, prior to use. To achieve such a separation and purification, conventional methods which use yeast fermentation, membrane filtration, fractional sedimentation, alkali treatment and/or column chromatography to separate and remove concomitant saccharides are arbitrarily chosen. In particular, column chromatography using strongly-acidic cation exchanges in salt form as disclosed in Japan Patent Kokai No. 23,799/83 and No. 148,794/84 is favorably feasible in the removal of concomitant saccharides so as to collect fractions which are rich in non-reducing tetra- and pentasaccharides or in non-reducing tetra-, penta- and hexasaccharides. In such a chromatography, fixed bed method, moving bed method and simulated moving bed method are arbitrarily practiceable. If necessary, these tetra-, penta- and hexasaccharides can be separately collected.

The alpha-D-oligoglucosyl alpha-D-oligoglucoside of this invention is a non-reducing oligosaccharide which is very stable, tasteless or low in sweetness, appropriately viscous and less or not susceptible to crystallization or readily soluble when in crystalline form. In addition the oligosaccharide of this invention is effective as a calorie source because it is susceptible to digesting enzymes and assimilable in vivo when orally ingested. Further the oligosaccharide of this invention is useful as saccharide sweetener material with a reduced sweetening power and cariogenicity because it is hardly fermentable by cariogenic microorganisms. Still further the oligosaccharide of this invention can be used along with amino acids and oligopeptides which readily cause a browning reaction with saccharides because it is chemically stable. Still further the oligosaccharide of this invention stabilizes biologically-active substances which readily lose their activity, as well as having an appropriate viscosity, reduced fermentability and properties of controlling osmotic pressure, imparting shapes and gloss, preventing crystallization of other saccharides and preventing retrogradation of amylaceous substances.

These properties of the alpha-D-oligoglucosyl alpha-D-oligoglucoside are favorably utilizable in the production of food products including foods, beverages, feeds and pet foods, as well as in the production of various composition including cosmetics, pharmaceuticals and shaped bodies. Alpha-D-oligoglucosyl alpha-D-oligoglucosides with a relatively low molecular weight according to this invention are low in sweetening power but usable intact as sweetening seasoning. Such an oligosaccharide can be used along with an appropriate amount of one or more other sweeteners, for example, powdered starch syrup, glucose, maltose, sucrose, isomerized sugar, honey, maple sugar, sorbitol, dihydrochalcone, stevioside, alpha-glycosyl stevioside, rebaudioside, glycyrrhizin, L-asparatyl-L-phenylalanine methyl ester, saccharin, glycine and alanine, as well as with a filler such as dextrin, starch and lactose, if necessary.

Powdered alpha-D-oligoglucosyl alpha-D-oligoglucosides can be used intact as filler, vehicle or binder or, if necessary, after mixing with other filler, vehicle and/or binder and successively shaping into granule, globe, short rod, plate, cube or tablet form because the powders are substantially non-hygroscopic, highly heat-resistant and very stable. Such a powder is favorably usable, for example, as materials for confectioneries and bakery products where flour, corn grits and starch are partially or wholly replaced with such a powder.

Further the alpha-D-oligoglucosyl alpha-D-oligoglucoside of this invention is favorably usable to sweeten foods and beverages in general as well as to improve their tastes and qualities because its taste well harmonizes with substances which have other types of tastes such as sour, salty, astringent, delicious and bitter tastes as well as because it is highly acid- and heat-resistant. For example, the oligosaccharide of this invention is favorably usable in a variety of seasonings such as soy sauce, powdered soy sauce, soy sauce powder, miso, miso powder, "moromi", "hishio", "furikake", mayonnaise, dressing, vinegar, "sanbai-zu", "funmatsu-sushi-su", "chuka-no-moto", "tent-suyu (soup for tenpura)", "mentsuyu (soup for Japanese-style noodles)", sauce, ketchup, "yakiniku-no-tare (soup for grilled meat)", curry roux, stew premix, soup premix, "dashi-no-moto", mixed seasoning, "mirin (heavily sweetened sake)", "shin-mirin (synthetic mirin)", table sugar and coffee sugar. In addition the oligosaccharide of this invention is favorably usable to sweeten, for example, Japanese-style confectioneries such as "senbei (rice crackers)", "arare (pellet-shaped senbei)", "okoshi (millet and rice cracker)", rice cake, "manju (bun with a bean-jam filling)", "uiro (sweet rice jelly)", "an (bean jam)", "yokan (sweet jelly of beans)", "mizu-yokan (soft adzuki-bean jelly)", "kingyoku", jelly, castella and "amedama (Japanese-style toffee)"; Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as those for fruit preserve and "kaki-gori (shaved ice)"; spreads and pastes such as flour paste, peanut paste and fruit paste; processed fruits and vegetables such as jam, marmalade, syrup-preserved fruit and crystallized fruit; pickled products such as "fukujin-zuke (sliced vegetables picked in soy sauce)", "bettara-zuke (fresh radish pickles)", "senmai-zuke" and "rakkyo-zuke (pickled shallots)"; premixes for pickled products such as "takuan-zuke-no-moto" and "hakusai-zuke-no-moto"; meat products such as ham and sausage; fish meat products such as fish meat ham, fish meat sausage, "kamaboko (boiled fish paste)", "chikuwa (literally bamboo wheels)" and "tenpura (deep fried foods)"; relishes such as "uni-no-shiokara (salted guts of sea urchin)", "ika-no-shiokara (salted guts of squid)", "su-konbu", "saki-surume" and "fugu-no-mirinboshi"; "tsukudani (food boiled down in soy sauce" such as those of "nori (dried seaweed)", "sansai (mountain vegetables)", "surume (dried squid)", small fish and shellfish; daily dishes such as "nimame (cooked beans)", potato salad and "konbu-maki (tangle roll)"; milk products; bottled and canned products such as those of meat, fish meat, fruit and vegetable; alcoholic drinks such as synthetic sake, liqueur, wine and whisky; beverages such as coffee, cocoa, juice, carbonated beverage, lactic acid beverage and lactobacillus beverage; premixes and instant foodstuffs such as pudding premix, hot cake premix, "sokuseki-shiruko (premix of adzuki-bean soup with rice cake)" and instant soup; baby foods; and therapeutic foodstuffs, as well as to improve their tastes and qualities.

Further the oligosaccharide of this invention can be used in feeds and pet foods for domestic animals and poultry including honey bee, silkworm and fish so as to improve their taste qualities. Still further the oligosaccharide of this invention is favorably usable as a sweetener for orally-usable products in solid, paste or liquid form including cosmetics and pharmaceuticals such as cigar, cigarette, dentifrice, lipstick, lip cream, internal medicine, troche, cod-liver oil drop, oral refreshing agent, cachou and gargle, in addition to uses as a taste quality-improving agent, taste-masking agent and quality-improving agent.

Still further the oligosaccharide of this invention is favorably usable as stabilizer, osmosis-controlling agent, vehicle, moisture-controlling agent, viscosity-controlling agent and quality-improving agent in the production of cosmetics, for example, soap, skin cream, body shampoo, hair cream, lip cream, skin refining agent and hair restorer.

The alpha-D-oligoglucosyl alpha-D-oligoglucoside of this invention is also favorably usable in the production of pharmaceuticals as a stabilizer for activities or active ingredients in biologically-active substances, for example, cytokines including interferon-alpha, interferon-beta, interferon-gamma, tumor necrosis factor-alpha, tumor necrosis factor-beta, macrophage-migration inhibitory factor, colony stimulating factor, transfer factor and interleukin 2; hormones such as insulin, growth hormone, prolactin, erythropoietin and follicle stimulating hormone; vaccines such as BCG vaccine, Japanese encephalitis vaccine, measles vaccine, poliomyelitis vaccine, vaccinia virus vaccine, tetanus toxoid, trimeresurus flavoviridis antivenom and human immunoglobulin; antibiotics such as penicillin, erythromycine, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease and glucanase; extracts such as ginseng extract, snapping turtle extract, chlorella extract, propolis extract and royal jelly; and viable microorganisms such as virus, lactobacillus, bifidobacterium and yeast, in addition to uses as osmosis-controlling agent, vehicle, intubation feeding and syrup agent. To incorporate the alpha-D-oligoglucosyl alpha-D-oligoglucoside of this invention in the aforementioned composition including foods, beverages, cosmetics, pharmaceuticals and shaped bodies, conventional methods, for example, mixing, kneading, dissolving, melting, soaking, permeating, spreading, applying, coating, spraying, injecting and solidifying are arbitrarily used before completion of their processing. The amount of the alpha-D-oligoglucosyl alpha-D-oligoglucoside to be incorporated is set to a level which allows the alpha-D-oligoglucosyl alpha-D-oligoglucoside to exhibit its characteristics, usually, 0.1% or more, desirably, 5% or more in products. The compositions thus obtained would find extensive uses, for example, in domestic, agricultural, forestry, fishery and chemical industrial products, as well as in foods, beverages, cosmetics and pharmaceutical which are perorally or parenterally used.

The following experiments will explain in detail this invention. In particular, Experiment A will explain at first the preparation, purification and characterization of a non-reducing saccharide-producing enzyme from Rhizobium species M-11, then illustrate the preparation of trehalose and non-reducing saccharides bearing a trehalose structure at their ends from reducing partial starch hydrolysates using the enzyme. While Experiment B will explain the preparation and physicochemical properties of several alpha-D-oligoglucosyl alpha-D-oligoglucosides according to this invention.

Experiment A-1
Production of non-reducing saccharide-producing enzyme in Rhizobium species M-11

A liquid culture medium consisting of 2.0 w/v % maltose, 0.5 w/v % pepton, 0.1 w/v % yeast extract, 0.1 w/v % disodium hydrogen phosphate, 0.1 w/v % potassium dihydrogen phosphate and water was adjusted to pH7.0. The liquid medium was divided into 100 ml aliquots which were then placed separately in 500 ml-flasks, sterilized at 120° C. for 20 minutes, cooled, inoculated with Rhizobium species M-11 (FERM BP-4130) and incubated at 27° C. and 130 rpm for 24 hours, thus obtaining a seed culture.

About 20 liters of a culture medium which had the same composition as used in the seed culture was placed in 30 l-jar fermenter, sterilized, cooled to 30° C., inoculated with 1 v/v % seed culture and incubated at 30° C. and pH6.0–8.0 for about 24 hours under aeration and agitation conditions. The enzymatic activity in the resultant culture was about 1.5 units/ml. A part of the culture was centrifugically separated into cells and supernatant and the former cells were then suspended in 50 mM phosphate buffer (pH7.0) to give the starting volume, followed by assaying the resultant cell suspension and supernatant for enzymatic activity. As the result, in the cell suspension about 0.6 units/ml of enzymatic activity was found, while about 0.9 units/ml of enzymatic activity was found in the supernatant.

The non-reducing saccharide-producing enzyme is assayed as follows: To 4 ml of 1.25 w/v % maltopentaose as substrate in 50 mM phosphate buffer (pH7.0) is added 1 ml of an enzyme solution and the mixture is incubated at 40° C. for 60 minutes, heated at 100° C. for 10 minutes to inactivate the enzyme, correctly diluted by 10-times in deionized water and determined for reducing power by the Somogyi-Nelson method. As control, a fresh preparation of the same enzyme solution is inactivated by heating at 100° C. for 10 minutes and then tested similarly as above. One unit of the enzyme is defined as the amount of enzyme that diminishes 1 micromole of reducing power in terms of the amount of maltopentaose for 1 minute under the above conditions.

Experiment A-2
Purification of enzyme

About 18 liters of the culture obtained in Experiment A-1 was treated with "MINI-LAB", a superhigh-pressure cell homogenizer commercialized by Dainippon Pharmaceutical Co., Ltd., Osaka, Japan, to crush cells. The resultant was centrifuged at 10,000 rpm for 30 minutes to obtain about 16 liters of supernatant. In the supernatant was dissolved ammonium sulfate to give a saturation degree of 0.2 and the resultant was allowed to stand at 4° C. for 1 hour and then centrifuged at 10,000 rpm for 30 minutes, followed by collecting a newly formed supernatant.

In the supernatant was further dissolved ammonium sulfate to give a saturation degree of 0.6 and the resultant was allowed to stand at 4° C. for 24 hours and then centrifuged at 10,000 rpm for 30 minutes, followed by collecting the resultant sediment. The sediment was dissolved in 10 mM phosphate buffer (pH7.0), dialyzed against a fresh preparation of the same buffer for 24 hours and centrifuged at 10,000 rpm for 30 minutes to remove insoluble substances. The dialyzed solution (360 ml) was divided into two portions which were then separately applied to ion exchange column chromatography using 300 ml "DEAE Toyo Pearl" gel, a product of Tosoh Corporation, Tokyo, Japan.

The objective enzyme, which had adsorbed on the gel, was eluted from the column with the same phosphate buffer additionally containing sodium chloride. The obtained enzyme-active fractions were dialyzed against the same phosphate buffer additionally containing 211 ammonium sulfate and centrifuged at 10,000 rpm for 30 minutes to remove insoluble substances and the resultant supernatant was applied to hydrophobic column chromatography using 300 ml "Butyl Toyo Pearl 650" gel, a product of Tosoh Corporation, Tokyo, Japan. The enzyme, which had adsorbed on the column, was eluted therefrom with a linear gradient decreasing from 2M to 0M, followed by collecting enzyme-active fractions. Thereafter the fractions were further applied to gel filtration chromatography using 300 ml "Toyo Pearl HW-55", a resin commercialized by Tosoh Corporation, Tokyo, Japan, and the enzyme-active fractions were collected. The enzymatic activities, specific activities and yields in particular purification steps were as shown in Table 1.

The purified enzyme preparation which had been obtained as eluate in the gel filtration step in Table 1 was determined for purity on electrophoresis using 7.5 w/v % polyacrylamide gel and the electrophoresis gave single protein band, confirming that the enzyme preparation was electrophoretically homogenous and highly pure.

TABLE 1

| Purification step | Enzyme activity (units) | Specific activity (units/mg protein) | Yield (%) |
| --- | --- | --- | --- |
| Culture | 26,800 | | 100 |
| Supernatant after cell crushing | 20,300 | 0.10 | 76 |
| Dialyzed solution after salting-out | 16,100 | 0.32 | 60 |
| Eluate from ion exchange column | 11,300 | 5.5 | 42 |
| Eluate from hydrophobic column | 5,730 | 98 | 21 |
| Eluate from gel filtration | 3,890 | 195 | 15 |

Experiment 3
Characterization of enzyme

A part of the purified enzyme preparation obtained in Experiment A-2 was subjected to SDS-polyacrylamide gel electrophoresis at a gel concentration of 10 w/v % and then determined for molecular weight by comparison with standard molecular markers commercialized by Nippon Bio-Rad Laboratories KK, Tokyo, Japan which had been electrophoresed on the same gel, revealing that the molecular weight of the enzyme was about 77,000–87,000 daltons.

Separately another part of the purified enzyme preparation was subjected to isoelectric point electrophoresis on polyacrylamide gel using 2 w/v % "Ampholine", a product of Pharmacia LKB, Upsala, Sweden, and then determined for isoelectric point by measuring pH in the electrophoresed gel, revealing that the isoelectric point of the enzyme was about 3.6–4.6.

Figure 1:
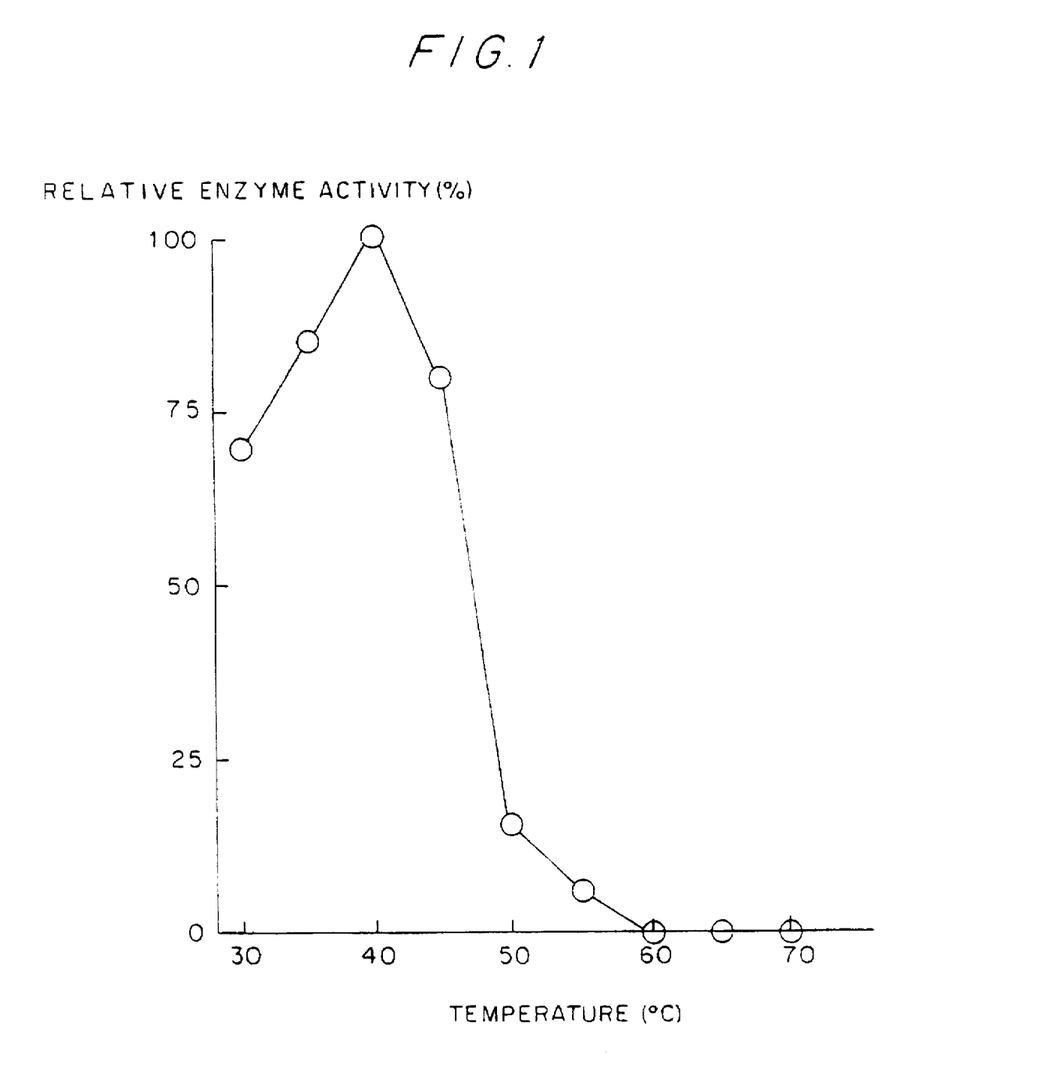
FIG. 1 illustrates the effect of temperature on the activity of non-reducing saccharide-producing enzyme from Rhizobium species M-11.
Figure 2:
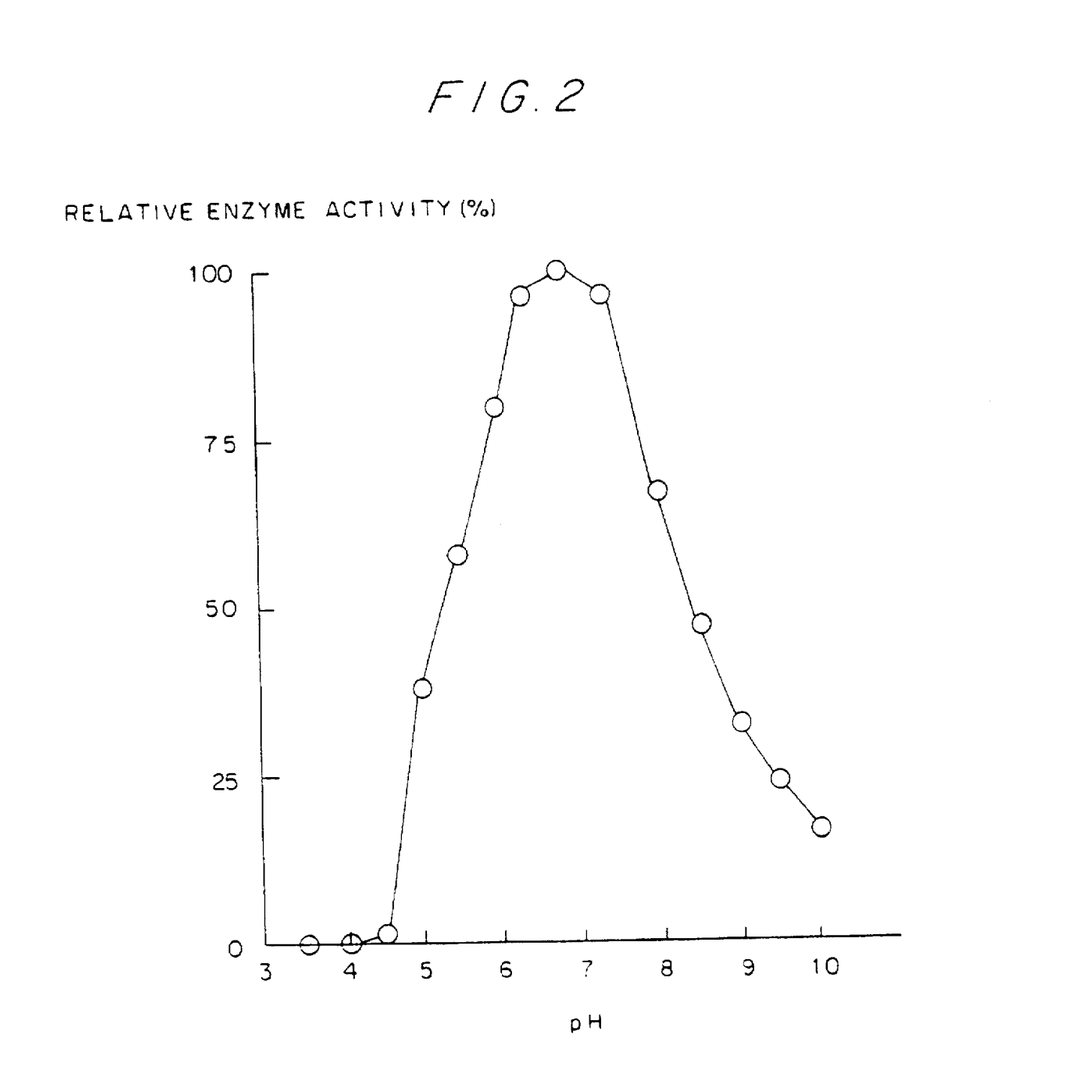
FIG. 2 illustrates the effect of pH on the activity of non-reducing saccharide-producing enzyme from Rhizobium species M-11.
Figure 3:
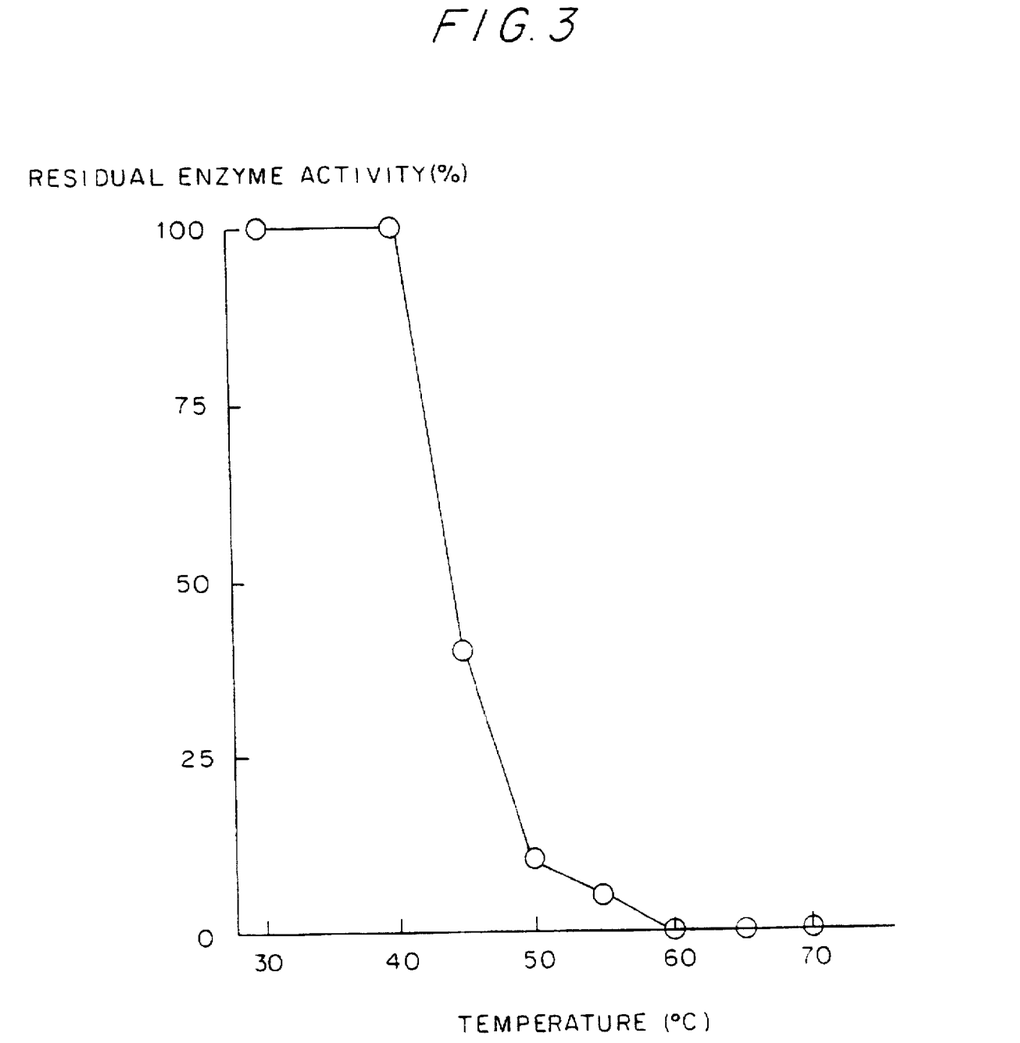
FIG. 3 illustrates the thermal stability of non-reducing saccharide-producing enzyme from Rhizobium species M-11.
Figure 4:
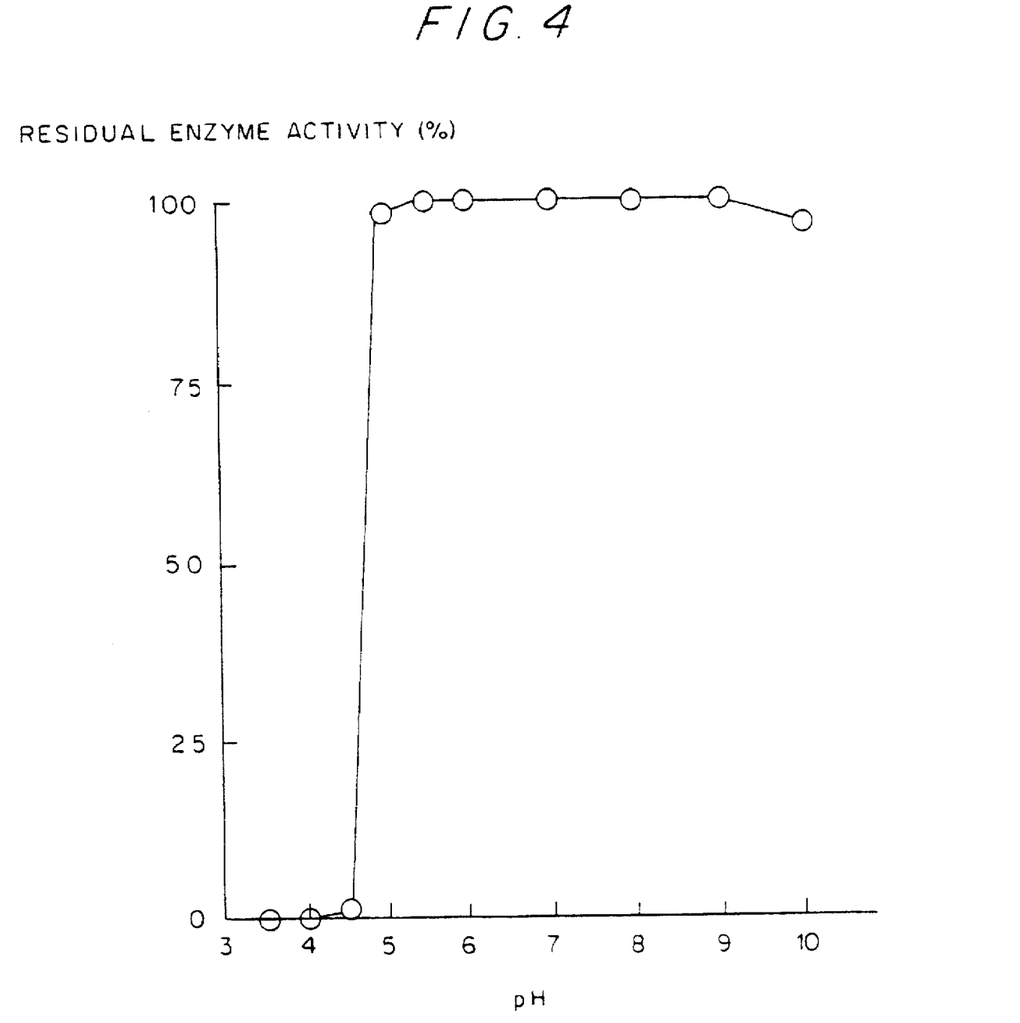
FIG. 4 illustrates the pH stability of non-reducing saccharide-producing enzyme from Rhizobium species M-11.

Effects of temperature and pH on enzymatic activity were tested in accordance with the aforementioned assay method. The results were as shown in FIGS. 1 and 2 respectively. The optimum temperature was found around 40° C. when incubated at pH7.0 for 60 minutes, while the optimum pH was about 7.0 when incubated at 40° C. for 60 minutes. Thermal stability of the enzyme was determined by incubating the enzyme in 50 mM phosphate buffer (pH7.0) at different temperatures for 60 minutes, cooling in water bath and assaying the residual enzymatic activities. While pH stability was determined by incubating the enzyme in 50 mM phosphate buffers at different pH levels and 25° C. for 16 hours, adjusting the buffers to pH7.0 and assaying the residual activities. The results were as shown in FIGS. 3 and 4 respectively. The enzyme was stable at a temperature up to 40° C. and at a pH in the range of about 6–9.

Experiment A-4
Preparation of non-reducing saccharide

Aqueous solutions containing 20 w/v % of either glucose, maltose, maltotriose, maltotetraose, maltopentaose, maltohexaose or maltoheptaose as substrate were added with 2 units/g substrate solid of the purified enzyme obtained in Experiment A-2 and reacted at 40° C. and pH7.0 for 48 hours and the resultants were deionized and analyzed for reaction products on high-performance liquid chromatography using "Wako Beads WB-T-330" column, a product of Wako Pure Chemical Industries, Ltd., Osaka, Japan. The high-performance liquid chromatography was carried out at room temperature and water as eluent was applied to the column at a flow rate of 0.5 ml/minute while monitoring eluates with "RI-8012", a differential refractometer commercialized by Tosoh Corporation, Tokyo, Japan. The results were as shown in Table 2.

As evident from the results in Table 2, the reaction products consisted of residual substrates and newly formed saccharides PI, PII, PIII, PIV and PV and no other saccharides were substantially detected. The yields for PII, PIII, PIV and PV, which had a glucose polymerization degree of 4 or higher, were relatively high, i.e. 85% or higher, while that for PI, which had a glucose polymerization of 3, was relatively low. It was revealed that no saccharides were formed from glucose and maltose.

TABLE 2

| Substrate | Reaction products | Elution time in HPLC (minutes) | Composition (%) |
| --- | --- | --- | --- |
| Glucose | Glucose | 33.4 | 100.0 |
| Maltose | Maltose | 28.5 | 100.0 |
| Maltotriose | PI + | 23.3 | 35.0 |
| | Maltotriose | 25.9 | 65.0 |
| Maltotetraose | PII + | 21.6 | 85.6 |
| | Maltotetraose | 24.1 | 14.4 |
| Maltopentaose | PIII + | 19.7 | 92.7 |
| | Maltopentaose | 22.6 | 7.3 |
| Maltohexaose | PIV + | 18.7 | 93.5 |
| | Maltohexaose | 21.4 | 6.5 |
| Maltoheptaose | PV + | 17.8 | 93.4 |
| | Maltoheptaose | 21.0 | 6.6 |

Note: PI, PII, PIII, PIV and PV in the Table designate the newly formed products from respective substrates, i.e maltotriose, maltotetraose, maltopentaose, maltohexaose, and maltoheptaose.

To purify these newly formed saccharides, the reaction products were decolored, deionized, concentrated and subjected to column fractionation using "XT-1016 (Na$^+$ form")", a strongly-acidic cation exchange in alkali metal from commercialized by Tokyo Organic Chemical Industries, Ltd., Tokyo, Japan. In particular, the cation exchange was packed in 3 jacketted and cascaded stainless steel columns, inner diameter of 2.0 cm, length of 1 m each, which were then loaded with either reaction product in an amount of 5 v/v % against the volume of the cation exchange and then applied with 55° C. water at SV 0.13 for fractionation, followed by collecting fractions which contained 97% or more newly formed saccharides. The obtained fractions were separately lyophilized into high-purity saccharide preparations. The yields against particular material substrates were about 9% for PI, about 65% for PII, about 82% for PIII, about 80% for PIV and about 77% for PV, on dry solid basis. The final purities were 97.5% for PI, 98.6% for PII, 99.5% for PIII, 98.4% for PIV and 98.4% for PV.

Thereafter these high-purity saccharide preparations were tested for reducing power with the Somogyi-Nelson method and their reducing powers were represented in terms of DE. The results were as shown in Table 3.

As evident from the results in Table 3, all the preparations exhibited very weak reducing powers. It was suggested that the reducing powers would be due to trace amounts of reducing maltooligosaccharides from the substrates which had been incorporated and present in the preparations, as well as that all the newly formed saccharides were substantially free from reducing power.

TABLE 3

| Saccharide preparation | Purity (%) | DE |
| --- | --- | --- |
| PI | 97.5 | 0.83 |
| PII | 98.6 | 0.35 |
| PIII | 99.5 | 0.10 |
| PIV | 98.4 | 0.27 |
| PV | 98.4 | 0.23 |

Experiment A-5
Enzymatic degradation using glucoamylase

Fifty milligrams of either non-reducing saccharide preparation PI, PII, PIII, PIV or PV prepared in Experiment A-4 was dissolved in 1 ml of 50 mM acetate buffer (pH4.5) and the resultant solutions were added with 1 unit of glucoamylase commercialized by Seikagaku Corporation, Tokyo, Japan, incubated at 40° C. for 6 hours for enzymatic degradation and analyzed for degradation products on high-performance liquid chromatography. As the result, only glucose and trehalose were detected in all the degradation products. The contents and molar ratios of glucose and trehalose were as shown in Table 4.

TABLE 4

| Saccharide preparation | Glucose (%) | Trehalose (%) | Molar ratio (Glucose/Trehalose) |
| --- | --- | --- | --- |
| PI | 36.2 | 63.8 | 1.07 |
| PII | 52.0 | 48.0 | 2.06 |
| PIII | 61.4 | 38.6 | 3.02 |
| PIV | 68.3 | 31.7 | 4.09 |
| PV | 72.9 | 27.1 | 5.11 |

As evident from the results in Table 4, it was revealed that PI was degraded by glucoamylase into 1 glucose molecule and 1 trehalose molecules; PII, into 2 glucose molecules and 1 trehalose molecule; PIII, into 3 glucose molecules and 1 trehalose molecule; PIV, into 4 glucose molecules and 1 trehalose molecule; and PV, into 5 glucose molecules and 1 trehalose molecule.

Considering the reaction characteristics of glucoamylase, these non-reducing saccharides would have a structure where glucose molecules are bound to trehalose molecule via the alpha-1,4 or alpha-1,6 linkage: In particular, PI is a non-reducing saccharide with a glucose polymerization degree of 3 where 1 glucose molecule is bound to 1 trehalose molecule; PII, a non-reducing saccharide with a glucose polymerization degree of 4 where 2 glucose molecules are bound to 1 trehalose molecule; PIII, a non-reducing saccharide with a glucose polymerization degree of 5 wherein 3 glucose molecules are bound to 1 trehalose molecule; PIV, a non-reducing saccharide with a glucose polymerization degree of 6 where 4 glucose molecules are bound to 1 trehalose molecule; and PV, a non-reducing saccharide with a glucose polymerization degree of 7 where 5 glucose molecules are bound to 1 trehalose molecule. After exposing PI, PII, PIII, PIV and PV to beta-amylase, PI and PII were not degraded, while PIII were degraded into 1 maltose molecule and one PI molecule; PIV, into 1 maltose molecule and one PII molecule; and PV, into 2 maltose molecules and one PI molecule.

The above results suggest that the reaction by non-reducing saccharide-producing enzyme according to this invention would be an intramolecular conversion reaction which does not accompany either degradation or polymerization of substrates, in other words, does not change their glucose polymerization degrees. Thus PI, PII, PIII, PIV and PV produced by the enzyme would be alpha-glucosyl trehaloses (as represented by "Gn-T" where "G" and "T" represent glucose residue and alpha,alpha-trehalose respectively, while "n" is an integer of 1 or more), in particular, alpha-glucosyl trehalose (or alpha-maltosyl glucoside), alpha-maltosyl trehalose (or alpha-maltotriosyl glucoside), alpha-maltotriosyl trehalose (or alpha-maltotetraosyl glucoside), alpha-maltotetraosyl trehalose (or alpha-maltopentaosyl glucoside) and alpha-maltopentaosyl trehalose (or alpha-maltohexaosyl glucoside) respectively.

Experiment A-6
Preparation of trehalose and non-reducing saccharide bearing trehalose structure at its end Forty parts by weight of "PINE-DEX #4", a partial starch hydrolysate commercialized by Matsutani Chemical Ind., Co., Ltd., Kyoto, Japan, was dissolved in 60 parts by weight of water while heating and the resultant solution was adjusted to 45° C. and pH6.5, added with 1 unit/g reducing partial starch hydrolysate of a non-reducing saccharide-producing enzyme prepared by the method in Experiment A-2 and reacted for 96 hours to form non-reducing saccharides bearing a trehalose structure at its end, followed by heating at 100° C. for 10 minutes to inactivate the enzyme. The reaction mixture was then diluted up to about 20%, added with 10 units/g partial starch hydrolysate of "Glucozyme", a glucoamylase commercialized by Nagase Biochemicals Ltd., Kyoto, Japan, reacted for 40 hours and heated to inactivate the enzyme. The resultant solution was decolored with activated carbon, deionized with ion exchanges and concentrated to about 60% in usual manner. The obtained saccharide solution contained 29.5% trehalose, on dry solid basis. This concentrate was then charged to a stainless steel column prepacked with "CG6000 (Na$^+$-form)", a strongly-acidic cation exchange commercialized by Japan Organo, Co., Ltd., Tokyo, Japan, at 60° C. and SV 0.4, and fractions which were rich in trehalose were collected. The fractions contained about 90% trehalose, on dry solid basis. The fractions were then concentrated to about 75%, fed in a crystallizer, added with about 2% crystalline trehalose hydrate as seed and gradually cooled to obtain a massecuit which had a crystallinity of about 45%. The massecuit was then sprayed from an upper part of a drying tower through a nozzle pressurized to 150 kg/cm$^2$. At the same time, 85° C. air was sent from an upper part of the drying tower towards its bottom and the crystalline powder which accumulated on a wire net of a conveyer provided at the bottom of the drying tower was gradually conveyed outside the drying tower while sending 45° C. air through the wire net towards the upper part of the drying tower. Thereafter the crystalline powder was fed to aging tower and aged in a stream of hot air for 10 hours to complete its crystallization and dehydration, thus obtaining crystalline trehalose hydrate powder.

Experiment B-1
Preparation of alpha-D-oligoglucosyl alpha-D-oligoglucoside

Fifty parts by weight of trehalose prepared by the method in Experiment A-6 and "PINE-DEX #1", a reducing partial starch hydrolysate (DE 8) commercialized by Matsutani Chemical Ind., Co., Ltd., Kyoto, Japan, were dissolved in 150 parts by weight of water while heating and the resultant solution was adjusted to 60° C. and pH6.0, added with a cyclemaltodextrin glucanotransferase from *Bacillus stearothermophilus* commercialized by Hayashibara Biochemical Laboratories, Inc., Okayama, Japan in an amount of 10 units/g reducing partial starch hydrolysate, reacted for 40 hours and heated at 100° C. for 30 minutes to inactivate the enzyme. The solution was then adjusted to 55° C. and pH5.0, added with "Beta-amylase #1500" commercialized by Nagase Biochemicals Ltd., Kyoto, Japan in an amount of 20 units/g reducing partial starch hydrolysate, reacted for 16 hours and heated at 100° C. for 15 minutes to inactivate the enzyme. The solution contained as alpha-D-oligoglucosyl alpha-D-oligoglucosides "Substance 1", "Substance 2" and "Substance 3" in respective amounts of about 15%, about 15% and about 4%, on dry solid basis. The solution was then decolored with activated carbon, deionized with ion exchanges (H$^+$- and OH$^-$-form), concentrated to about 45% and applied to column chromatography, followed by collecting fractions which were rich in Substances 1, 2 and 3. The ion exchange for fractionation was "XT-1016 (Na$^+$ form)", a strongly-acidic cation exchange in salt form commercialized by Japan Organo, Co., Ltd., Tokyo, Japan, which was packed in aqueous suspension form in four jacketted stainless steel columns, inner diameter of 5.4 cm, length of 5 m each. In this case, the four columns were cascaded to give a total length of about 20 m. While keeping the temperature in the columns at 55° C., the columns were charged with 5 v/v % material saccharide solution and then applied with 55° C. water at SV 0.3 for fractionation, followed by collecting fractions which were rich in Substances 1, 2 and 3. The fractions were further applied to a preparative liquid chromatography using both "YMC-Pack R-355-15", a column for preparative liquid chromatography packed with octadecyl silica gel as carrier commercialized by YMC Co., Ltd., Kyoto, Japan and also using water as eluent, and fractions which had a purity of 97% or higher were collected, lyophilized and pulverized to obtain high-purity Substances 1, 2 and 3 in powder form.

Experiment B-2

Physicochemical properties of alpha-D-oligoglucosyl alpha-D-oligoglucoside

Using high-purity Substances 1, 2 and 3 prepared by the method in Experiment B-1, the following physicochemical properties were determined.

(1) Elemental analysis Substance 1 Found: C=44.3%, H=6.2% Calculated: C=43.25%, H=6.35% (for molecular formula: $C_{24}H_{42}O_{21}$) Substance 2 Found: C=43.7%, H=6.0% Calculated: C=43.48%, H=6.32% (for molecular formula: $C_{30}H_{52}O_{26}$) Substance 3 Found: C=43.8%, H=6.1% Calculated: C=43.64%, H=6.31% (for molecular formula: $C_{36}H_{62}O_{31}$)

(2) Molecular weight

Substance 1 666.6
Substance 2 828.7
Substance 3 990.9

(3) Ultraviolet absorption

These three substance exhibited no characteristic absorption.

(4) Coloring reaction

These three substances colored green upon the anthrone-sulfuric acid reaction but were negative to both Fehling's reaction and iodine reaction.

(5) Structure (a) Upon hydrolysis by 1N sulfuric acid, these three substances formed D-glucose as sole product.

(b) When exposed to glucomylase, Substance 1 formed 2 moles of glucose and 1 mole of trehalose; Substance 2, 3 moles of glucose and 1 mole of trelhalose; and Substance 3, 4 moles of glucose and 1 mole of trehalose.

(c) Carbon nuclear resonance analysis ($^{13}$C-NMR) gave distinct twelve $^{13}$C signals for

Substance 1. This revealed that Substance 1 bore 24 carbon atoms, as well as the presence of 12 pairs of 2 equivalent carbon atoms. By assigning these carbon atoms with reference to the chemical shifts reported in Klaus Bock et al., Advances in Carbohydrate Chemistry and Biochemistry, Vol.42, pp.192–225 (1984) for alpha-D-glucopyranose, alpha,alpha-trehalose and maltose as standard substances, it was suggested that Substance 1 had a structure represented by O-alpha-D-glucopyranosyl-(1→4)-alpha-D-glucopyranosyl alpha-D-maltoside.

Substance 2 gave distinct nineteen $^{13}$C signals. It was revealed that Substance 2 beared 30 carbon atoms and the presence of 7 pairs of 2 equivalent carbon atoms and one set of 5 equivalent carbon atoms. By assigning these carbon atoms with reference to the chemical shifts reported by Klaus Bock et al. similarly as in Substance 1, it was suggested that Substance 2 had a structure represented by O-alpha-D-glucopyranosyl-(1→4)-O-alpha-D-glucopyranosyl-(1→4)-alpha-D-glucopyranosyl alpha-D-maltoside.

Substance 3 gave distinct sixteen $^{13}$C carbon signals. It was revealed that Substance 3 beared 36 carbon atoms and the presence of 15 pairs of 2 equivalent carbon atoms and one set of 6 equivalent carbon atoms. By assigning these carbon atoms with reference to the chemical shifts reported by Klaus Bock et al. similarly as in Substance 1, it was suggested that Substance 3 had a structure represented by O-alpha-D-glucopyranosyl-(1→4)-O-alpha-D-glucopyranosyl-(1→4)-alpha-D-glucopyranosyl alpha-D-maltotrioside.

Based on the above results, the structures of Substances 1, 2 and 3 can be represented by Chemical formulae 1, 2 and 3 respectively.

Chemical formula 1:

Chemical formula 2:

Chemical formula 3:

Because of these structures, Substances 1, 2 and 3 were designated as "alpha-D-maltosyl alpha-D-maltoside (or maltosyl maltoside)", "alpha-D-maltotriosyl alpha-D-maltoside (or maltotriosyl maltoside)" and "alpha-D-maltotriosyl alpha-D-maltotrioside (or maltotriosyl maltotrioside)" respectively. The above results suggest that these substances would be hitherto unknown, entirely novel non-reducing oligosaccharides which bear a trehalose structure in the molecules.

Experiment B-3
Acute toxicity

High-purity maltosyl maltoside, maltotriosyl maltoside and maltotriosyl maltotrioside prepared by the method in Experiment B-1 were tested for acute toxicity in mice upon oral administration. As the result, maltosyl maltoside, maltotriosyl maltoside and maltotriosyl maltotrioside were found to be low intoxicity and no death was observed with their maximum administrable dose. These suggest that their $LD_{50}$ would be briefly 50 g/kg or higher.

Experiment B-4
Preparation and physicochemical properties of crystalline alpha-D-maltotriosyl alpha-D-maltotrioside An alpha-D-maltotriosyl alpha-D-maltotrioside (Substance 3), purity of 97% or higher, prepared by the method in Experiment B-1, was decolored, deionized and concentrated to 70% in usual manner and the concentrate was transferred in a beaker and allowed to stand in 4° C. chilled room for 2 months leading to eduction of crystals. The crystals were centrifugally collected and washed with a minimum amount of water, thus obtaining crystals with a purity of 99.0%.

The physicochemical properties of the crystals as tested were as follows:

(1) Color

Colorless, transparent crystal (2) Solubility

Relatively high, about 91 g being soluble in 100 ml of 25° C. water.

(3) Melting point

215° C.

(4) Infrared absorption spectrum

Figure 5:
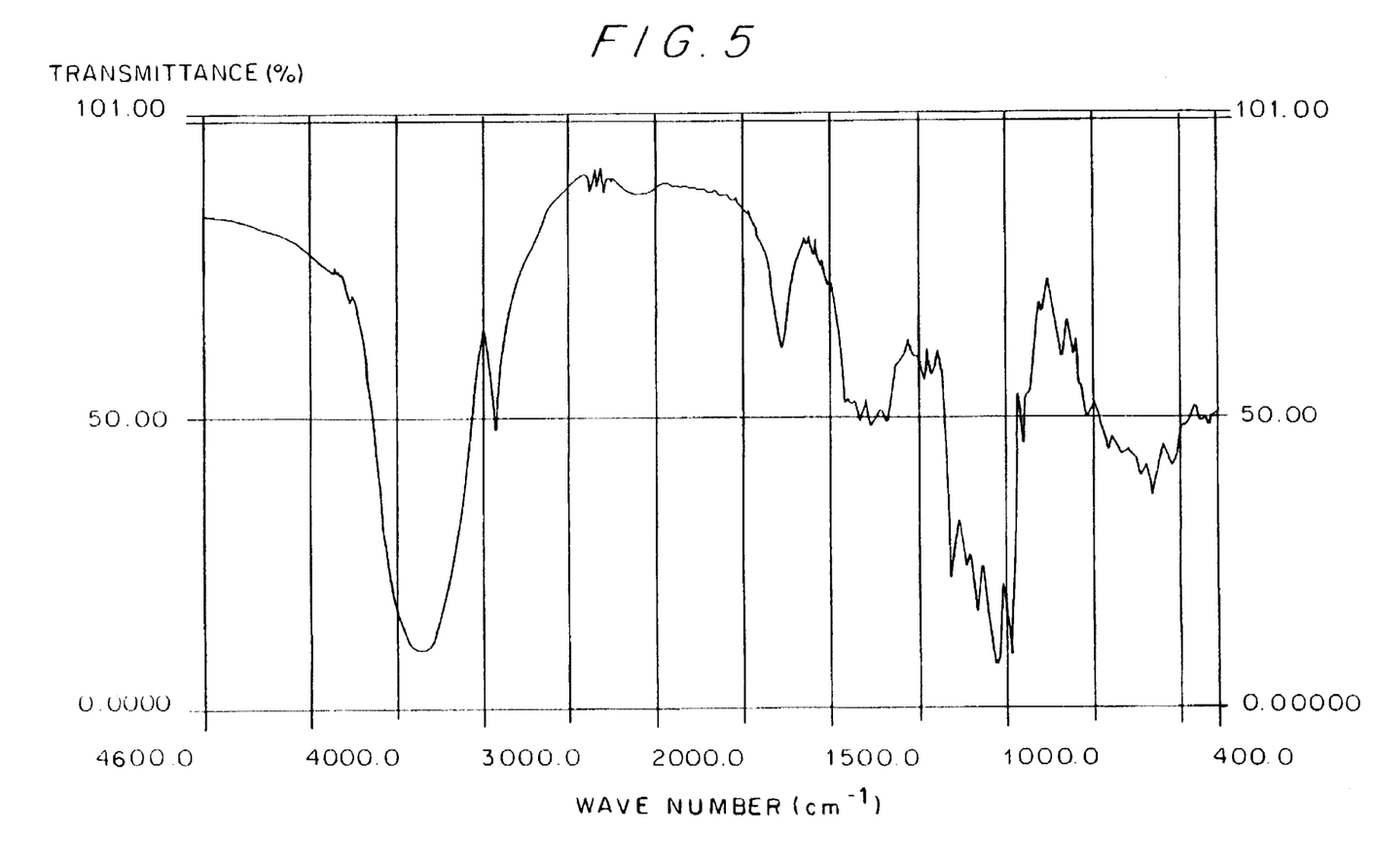
FIG. 5 is the infrared absorption spectrum of crystalline alpha-D-maltotriosyl alpha-D-maltotrioside.

One milligram of powdered crystal and 200 mg of dried KBr were mixed and prepared into a transparent tablet which was then analyzed for infrared absorption spectrum. The result was as shown in FIG. 5.

(5) Powder x-ray diffraction

Figure 6:
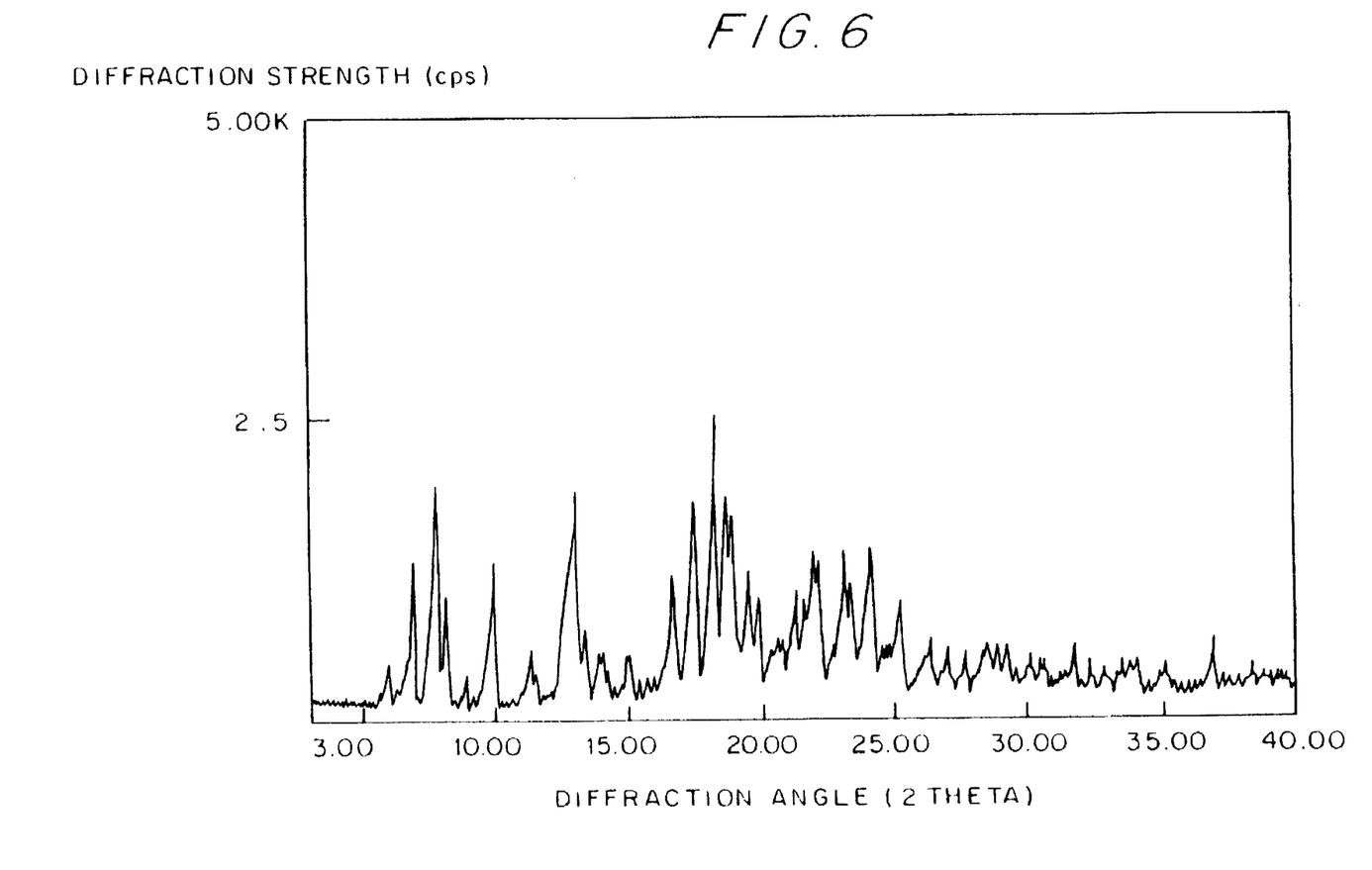
FIG. 6 is the powder x-ray diffraction figure of crystalline alpha-D-maltotriosyl alpha-D-maltotrioside.

Crystalline alpha-D-maltotriosyl alpha-D-maltotrioside was determined for powder x-ray diffraction figure using CuKalpha-ray in accordance with the method reported in F. H. Stodola et al., *Journal of the American Chemical Society*, Vol.78, pp.2,514–2,518 (1956). The results were as shown FIG. 6. As evident from the results in FIG. 6, crystalline alpha-D-maltotriosyl alpha-D-maltotrioside gave predominant diffraction angles (2 theta) of 7.8°, 10.0°, 13.1°, 17.5° and 18.2° on powder x-ray diffraction analysis.

The above results suggest that the crystal would be of a novel crystalline alpha-D-maltotriosyl alpha-D-maltotrioside.

Any methods can be used in this invention as long as they enable the eduction and collection of crystalline alpha-D-maltotriosyl alpha-D-maltotrioside from supersaturated solutions, and conventional methods, for example, massecuite-separation method, block pulverization method, fluidized-bed granulation method and spray drying method, are arbitrarily chosen. The crystalline alpha-D-maltotriosyl alpha-D-maltotrioside exhibits a very weak hygroscopicity which varies depending on the purity of alpha-D-maltotriosyl alpha-D-maltotrioside but is favorably usable in a variety of compositions, for example, those for foods, beverages, cosmetics, pharmaceuticals, shaped bodies and chemical materials because it is substantially non-hygroscopic, free flowing, free of adhesion and solidification and easily handleable. The melting point and specific rotation of crystalline alpha-D-maltotriosyl alpha-D-maltotrioside vary dependently on its purity. In particular, the melting point usually decreases and widens as purity decreases. Thus the purity of crystalline alpha-D-maltotriosyl alpha-D-maltotrioside can be arbitrarily chosen to meet to needs in its final uses.

The following Example A and Example B will illustrate the production of alpha-D-oligoglucosyl alpha-D-oligoglucoside and several uses of the same respectively.

EXAMPLE A-1

One part by weight of trehalose prepared by the method in Experiment A-6 and 2 parts by weight of "PINE-DEX #4", a dextrin product (DE 18) commercialized by Matsutani Chemical Ind., Co., Ltd., Kyoto, Japan, were dissolved in 3.7 parts by weight of water while heating, and the resultant solution was adjusted to 60° C. and pH5.6, added with 15 units/g dextrin of a cyclomaltodextrin glucanotransferase from *Bacillus stearothermophilus* commercialized by Hayashibara Biochemical Laboratories, Inc., Okayama, Japan, reacted for 24 hours and heated to inactivate the enzyme. Thereafter the solution was decolored with activated carbon, deionized and purified with ion exchanges ($H^+$- and $OH^-$-form) and concentrated in usual manner to obtain 75% syrup in the yield of about 92%, on dry solid basis.

The product, which contains about 65% non-reducing oligosaccharides such as maltosyl maltoside, maltotriosyl maltoside, maltotriosyl maltotrioside, maltotetraosyl maltotrioside and maltotetraosyl maltotetraoside, on dry solid basis, has a reduced sweetness, appropriate viscosity and moisture-retaining activity which render the product very useful in a variety of compositions including foods, beverages, cosmetics, pharmaceuticals and shaped bodies.

EXAMPLE A-2

One part by weight of trehalose commercialized by Wako Pure Chemical Industries, Ltd., Osaka, Japan and 1.5 parts by weight of alpha-cyclodextrin were dissolved in 4 parts by weight of water while heating, and the resultant solution was adjusted to 65° C. and pH 5.6, added with 10 units/g alpha-cyclodextrin of the same type of cyclomaltodextrin glucanotransferase as used in Example A-1, reacted for 24 hours and heated to inactivate the enzyme. The solution was then adjusted to 55° C. and pH5.6, added with 20 units/g solid of "Beta-amylase #1500" commercialized by Nagase Biochemicals Ltd., Kyoto, Japan, reacted for 16 hours and heated to inactivate the enzyme. The resultant was purified and concentrated similarly as in Example A-1 to obtain 75% syrup in the yield of about 93%, on dry solid basis.

The product, which contains maltosyl maltoside, maltotriosyl maltoside and maltotriosyl maltotrioside in respective amounts of about 15%, about 15% and about 4%, on dry solid basis, has a reduced sweetness, appropriate viscosity and moisture-retaining activity as the product in Example A-1 which render the product very useful in a variety of compositions including foods, beverages, cosmetics, pharmaceuticals and shaped bodies.

EXAMPLE A-3

A 20% starch suspension was added with "Termamyl 60 L", an alpha-amylase commercialized by Novo Nordisk Industry, Copenhagen, Denmark, in an amount of 0.015% with respect to starch solid, liquefied at 95°–100° C. and heated to inactivate the enzyme, thus obtaining a liquefied starch solution with DE 3. The solution was added with trehalose prepared by the method in Experiment A-6 in the same amount as that of amylaceous substance, on dry solid basis, adjusted to 55° C. and pH5.3, added with 50 units/g starch of an isoamylase commercialized by Hayashibara Biochemical Laboratories, Inc., Okayama, Japan and 10 units/g starch of the same type of cyclomatodextrin glucanotransferase as used in Example A-1, reacted for 40 hours and heated to inactivate the enzymes. The solution was then diluted to about 25% by addition of water, adjusted to 55° C. and pH5.3, added with 20 units/g solid of beta-amylase, reacted for 16 hours and heated to inactivate the enzyme. Thereafter the solution was purified and concentrated similarly as in Example A-1 and spray-dried in usual manner to obtain 75% syrup with a moisture content less than about 2% in the yield of about 90%, on dry solid basis.

The product, which contains maltosyl maltoside, maltotriosyl maltoside and maltotriosyl maltotrioside in respective amounts of about 20%, about 20% and about 6%, on dry solid basis, has a reduced sweetness, appropriate viscosity and moisture-retaining activity as the product in Example A-1 which render the product very useful in a variety of compositions including foods, beverages, cosmetics, pharmaceuticals and shaped bodies.

EXAMPLE A-4

A material saccharide solution which contained maltosyl maltoside, maltotriosyl maltoside and maltotriosyl maltotrioside prepared by the method in Example A-2 was concentrated to about 45%. To elevate the contents of maltosyl maltoside, maltotriosyl maltoside and maltotriosyl maltotrioside, the solution was chromatographed similarly as in Experiment B-1 except that the ion exchange for fractionation was replaced with "Dowex 50WX4 ($Ca^{2+}$ form)", a strongly-acidic cation exchange in salt form commercialized by the Dow Chemical Co., Midland, Mich., USA, and fractions which were rich in maltosyl maltoside, maltotriosyl maltoside and maltotriosyl maltotrioside were collected, purified and concentrated similarly as in Example A-1 to obtain 65% syrup in the yield of about 45%, on dry solid basis.

The syrup, which contains maltosyl maltoside, maltotriosyl maltoside and maltotriosyl maltotrioside in respective amounts of about 35%, about 35% and about 10%, on dry solid basis, has a reduced sweetness, appropriate viscosity and moisture-retaining activity as the product in Example A-1 which renders the syrup very useful in a variety of compositions including foods, beverages, cosmetics, pharmaceuticals and shaped bodies.

EXAMPLE A-5

A material saccharide solution which contained maltosyl maltoside, maltotriosyl maltoside and maltotriosyl maltotrioside prepared by the method in Example A-3 was concentrated to about 50%. The concentrate was then chromatographed in accordance with the method in Experiment B-1, and fractions which were rich in either maltosyl maltoside, maltotriosyl maltoside or maltotriosyl maltotrioside were collected, purified and concentrated similarly as in Example A-1 to obtain 65% syrups in respective yields of about 15%, about 15% and about 4%, on dry solid basis.

The syrups, which contain about 97% high-purity maltosyl maltoside, maltotriosyl maltoside or maltotriosyl maltotrioside, on dry solid basis, have a reduced sweetness, appropriate viscosity and moisture-retaining activity as the product in Example A-1 which render the syrups very useful in a variety of compositions including foods, beverages, cosmetics, pharmaceuticals and shaped bodies.

EXAMPLE A-6

A high-purity maltotriosyl maltotrioside obtained by the method in Example A-5 was concentrated to about 85%, fed to crystallizer, added with 2% crystalline maltotriosyl maltotrioside as seed, gradually stirred for crystallization, transferred to baths and allowed to stand at room temperature for 2 days to complete crystallization and ageing and the contents in block form were fed to pulverizer, dried and sieved to obtain a crystalline maltotriosyl maltotrioside powder.

The product is substantially non-hygroscopic and easily handleable. Further the product is favorably usable in a variety of compositions including foods, beverages, cosmetics, pharmaceuticals and shaped bodies because it has a superior solubility and stability, reduced sweetness, appropriate viscosity and moisture-retaining activity.

EXAMPLE A-7

A 20% saccharide mixture solution which contained non-reducing oligosaccharides bearing a trehalose structure at their ends prepared by the method in Experiment A-6 was added with 10 units/g solid of cyclomaltodextrin glucanotransferase, reacted for 24 hours and heated to inactivate the enzyme. The solution was then adjusted to 55° C. and pH5.3, added with 20 units/g dextrin of beta-amylase, reacted for 16 hours and heated to inactivate the enzyme. Thereafter the solution was purified and concentrated similarly as in Example A-1 to obtain 75% syrup in the yield of about 92%, on dry solid basis.

The syrup, which contains maltosyl maltoside, maltotriosyl maltoside and maltotriosyl maltotrioside in respective amounts of about 25%, about 25% and about 8%, on dry solid basis, has a reduced sweetness, appropriate viscosity and moisture-retaining activity as the product in Example A-1 which render the syrup very useful in a variety of compositions including foods, beverages, cosmetics, pharmaceuticals and shape bodies.

EXAMPLE A-8

A syrup with elevated maltosyl maltoside, maltotriosyl maltoside and maltotriosyl maltotrioside contents, prepared by the method in Example A-4, was spray-dried in usual manner to obtain a powder with a moisture content of about 1% in the yield of about 90%.

Like the product in Example A-1, the powder is favorably usable in a variety of compositions including foods, beverages, cosmetics, pharmaceuticals and shaped bodies.

EXAMPLE A-9

A high-purity maltosyl maltoside syrup prepared by the method in Example A-5 was lyophilized at 60° C. for 24 hours. The obtained dried product was applied to pulverizer to obtain a powder with a moisture content of about 0.5% in the yield of about 93%.

Like the product in Example A-1, the powder is favorably usable in a variety of compositions including foods, beverages, cosmetics, pharmaceuticals and shaped bodies.

EXAMPLE B-1
Sweetener

One part by weight of a crystalline maltotriosyl maltotrioside powder obtained by the method in Example A-6 and 0.05 parts by weight of "alpha G Sweet", an alpha-glycosyl stevioside commercialized by Toyo Sugar Refining Co., Ltd., Tokyo, Japan, were mixed to homogeneity and the mixture was fed to granulater to obtain a granular sweetener.

The sweetener has a superior taste quality and about 2-fold stronger sweetening power and the calorie in terms of sweetening power is about one half in comparison with sucrose.

The sweetener is suitable to sweeten low-calorie foods and beverages for those with obesity or diabetes whose calorie intakes are restricted. Further the sweetener is also suitable to sweeten foods and beverages which are directed to suppress dental caries because it is less in acid and insoluble glucan production by cariogenic microorganisms.

EXAMPLE B-2
Hard candy

One hundred parts by weight of 55% sucrose solution and 30 parts by weight of a syrup containing non-reducing oligosaccharides such as maltosyl maltoside, maltotriosyl maltoside and maltotriosyl maltotrioside obtained by the method in Example A-1 were mixed while heating, and the mixture was concentrated to a moisture content lower than 2% by heating in vacuo, added with 1 part by weight of citric acid and appropriate amounts of lemon flavor and coloring agent and shaped in usual manner.

The product is a high-quality hard candy which is crisp, superior in taste quality and free of crystallization of sucrose.

EXAMPLE B-3
Strawberry jam

One hundred and fifty parts by weight of fresh strawberry, 60 parts by weight of sucrose, 20 parts by weight of maltose, 40 parts by weight of a syrup containing maltosyl maltoside, maltotriosyl maltoside and maltotriosyl maltotrioside obtained by the method in Example A-2, 5 parts by weight of pectin and 1 part by weight of citric acid were boiled down in a pot and the resultant was bottled.

The product is a jam which is superior in flavor and color.

EXAMPLE B-4
Lactic acid drink

Ten parts by weight of defatted milk was pasteurized at 80° C. for 20 minutes, cooled to 40° C., added with 0.3 parts by weight of starter and fermented at about 37° C. for 10 hours. The resultant was homogenized, added with 4 parts by weight of a powder containing maltosyl maltoside, maltotriosyl maltoside and maltotriosyl maltotrioside obtained by the method in Example A-8, 1 part by weight of sucrose and 2 parts by weight of isomerized sugar and the mixture was pasteurized by keeping it at 70° C. Thereafter the mixture was cooled, added with an appropriate amount of flavoring agent and bottled.

The product is a high-quality lactic acid drink where flavor and sweetness well harmonize with sour taste.

EXAMPLE B-5
Sweetened condensed milk

In 100 parts by weight of fresh milk was dissolved 3 parts by weight of a syrup containing non-reducing oligosaccharides such as maltosyl maltoside, maltotriosyl maltoside and maltotriosyl maltotrioside obtained by the method in Example A-1 and 1 part by weight of sucrose, and the resultant solution was sterilized by heating with plate heater, concentrated to about 70% and sterilely canned.

The product is favorably usable in body foods and seasonings for fruits, coffee, cocoa and tea because it has a mild sweetness and superior flavor.

EXAMPLE B-6
Powdered juice

Thirty-three parts by weight of spray-dried orange juice was mixed with 50 parts by weight of a high-purity maltosyl maltoside powder obtained by the method in Example A-9, 10 parts by weight of sucrose, 0.65 parts by weight of citric anhydride, 0.1 part of malic acid, 0.1 parts by weight of L-ascorbic acid, 0.1 part by weight of sodium citrate, 0.5 parts by weight of pullulan and an appropriate amount of powdered flavoring agent to homogeneity, pulverized into a fine powder, fed to fluidized bed granulator and granulated at a ventilation temperature of 40° C. for 30 minutes while spraying as binder a syrup with high maltosyl maltoside, maltotriosyl maltoside and maltotriosyl maltotrioside contents, obtained by the method in Example A-4, over the powder, followed by dividing into a prescribed amount and packaging.

The product is a powdered juice which has a natural fruit juice content of about 30%. The product is free of undesirable taste and smell, moisture intake and solidification and very stable over an extended time period.

EXAMPLE B-7
Chocolate

Forty parts by weight of cacao paste, 10 parts by weight of cacao butter, 30 parts by weight of sucrose and 20 parts by weight of a high-purity maltosyl maltoside powder obtained by the method in Example A-9 were mixed, and the resultant mixture was fed to refiner to reduce particle size, fed to conche and kneaded at 50° C. for 2 days. During the kneading, the mixture was added with 0.5 parts by weight of lecithine and sufficiently mixed and dispersed. Thereafter the mixture was adjusted to 31° C. with thermocontroller, poured in molds immediately before solidification of the butter, deaerated with vibrator and passed through 10° C. cooling tunnel over 20 minutes to complete solidification. The contents in the molds were then taken out and packaged.

The product, which has a superior color, gloss and texture but has no hygroscopicity, smoothly melted in the mouth to exhibit a gentle sweetness and mild flavor.

EXAMPLE A-8
Chewing gum

Three parts by weight of gum base was softened by heating, added with 4 parts by weight of sucrose and 3 parts by weight of a powder containing maltosyl maltoside, maltotriosyl maltoside and maltotriosyl maltotrioside obtained by the method in Example A-8, mixed with appropriate amounts of flavoring and coloring agents, kneaded with roller, shaped and packaged in usual manner.

The product is a chewing gum with a superior texture, flavor and taste.

EXAMPLE B-9

Custard cream

One hundred parts by weight of cornstarch, 100 parts by weight of a powder containing maltosyl maltoside, maltotriosyl maltoside and maltotriosyl maltotrioside obtained by the method in Example A-3, 80 parts by weight of maltose, 20 parts by weight of sucrose and 1 part by weight of sodium chloride were mixed to homogeneity, and the resultant mixture was added with 280 parts of fresh egg, mixed by stirring, gradually added with 1,000 parts by weight of boiling milk, heated while stirring until the cornstarch was gelatinized and the mixture wholly became semitransparent, cooled, added with an appropriate amount of vanilla flavor, divided into prescribed amount and packaged.

The product has a smooth gloss, mild sweetness and delicious taste.

EXAMPLE B-10

"Uiro-no-moto (instant "uiro"))"

Ninety parts by weight of rice powder was mixed with 20 parts by weight of cornstarch, 120 parts by weight of a high-purity maltosyl maltoside powder obtained by the method in Example A-9 and 4 parts by weight of pullulan to homogeneity to obtain "uiro-no-moto". The "uiro-no-moto" was kneaded with appropriate amounts of "maccha (a green tea)" and water and the resultant was divided in vessels and steamed for 60 minutes to obtain "maccha-uiro".

The product is superior in gloss and biting properties. Further the product has a long shelf life because retrogradation of starch is effectively suppressed.

EXAMPLE B-11

Milky lotion

One half part by weight of polyoxyethylene behenyl ether, 1 part by weight of polyoxyethylene sorbitol tetraoleate, 1 part by weight of oil-soluble glyceryl monostearate, 0.5 parts by weight of behenyl alcohol, 1 part by weight of avocado oil, 3.5 parts by weight of a syrup containing maltosyl maltoside, maltotriosyl maltoside and maltotriosyl maltotrioside obtained by the method in Example A-7, 1 part by weight of alpha-glycosyl rutin and appropriate amounts of vitamin E and germicidal agent were dissolved in usual manner by heating, and the mixture was added with 5 parts by weight of 1,3-butylene glycol, 0.1 part by weight of carboxyvinyl polymer and 85.3 parts by weight of refined water and emulsified with homogenizer.

The product is a moisture-retaining milky lotion which is favorably usable as sunscreen agent and skin-whitening agent.

EXAMPLE B-12

Skin cream

Two parts by weight of polyoxylethylene glycol monostearate, 5 parts by weight of self-emulsifying glycerine monostearate, 2 parts by weight of alpha-glycosyl rutin, 1 part by weight of liquid paraffin, 10 parts by weight of glyceryl trioctanate, 4 parts by weight of a high-purity maltosyl maltoside powder obtained by the method in Example A-9 and an appropriate amount of antiseptic were dissolved in usual manner by heating, and the resultant solution was added with 5 parts by weight of 1,3-butylene glycol and 66 parts by weight of refined water, emulsified with homogenizer and admixed with an appropriate amount of flavoring agent by stirring.

The product is a well-spreading cream which is favorably usable as sunscreen cream, skin-refining agent and skin-whitening agent.

EXAMPLE B-13

Detifrice

Forty-five parts by weight of calcium hydrogen phosphate, 1.5 parts by weight of sodium laurate, 25 parts by weight of glycerine, 0.5 parts by weight of polyoxyethylene sorbitan laurate, 15 parts by weight of a syrup with elevated maltosyl maltoside, maltotriosyl maltoside and maltotriosyl maltotrioside contents obtained by the method in Example A-4, 0.02 parts by weight of saccharin and 0.05 parts by weight of antiseptic were mixed with 13 parts by weight of water.

The product, which is superior in gloss and detergency, is suitable as dentifrice.

EXAMPLE B-14

Intubation feeding

A composition consisting of 20 parts by weight of a powder containing maltosyl maltoside, maltotriosyl maltoside and maltotriosyl maltotrioside obtained by the method in Example A-8, 1.1 part by weight of glycine, 1 part by weight of sodium glutamate, 0.4 parts by weight of calcium lactate, 0.1 part by weight of magnesium carbonate, 0.01 part by thiamine and 0.01 part by weight of riboflavin was divided into 24 g aliquots in small laminated aluminum packs which were then heat-sealed.

One pack of the product is dissolved in about 33– 500 ml water, prior to parenteral administration to the nasal cavity, stomach or intestine.

The product is favorably usable as intubation feeding for domestic animals through parenteral route, as well as for humans.

EXAMPLE B-15

Itubation feeding

A composition consisting of 580 parts by weight of a crystalline maltotriosyl maltotrioside powder obtained by the method in Example A-6, 190 parts by weight of dried yolk, 209 parts by weight of defatted milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 parts by weight of vitamin E acetate and 0.04 parts by weight of nicotin amide was divided into 25 g aliquots in small laminated aluminum packs which were then heat-sealed.

One pack of the product is dissolved in about 150–300 ml water, prior to parenteral administration to the nasal cavity, stomach or intestine.

EXAMPLE B-16

Liquid interferon agent

A natural human interferon-gamma preparation produced by Hayashibara Biochemical Laboratories, Inc., Okayama, Japan and commercialized by Cosmo Bio Co., Ltd., Tokyo, Japan was applied in usual manner to immobilized an anti-human interferon-gamma antibody column to adsorb thereon the natural human interferon-gamma in the preparation but to pass the calf serum albumin as stabilizer through the column for removal, and the adsorbed natural human interferon-gamma was eluted by applying to the column a physiological saline containing a high-purity maltosyl maltoside syrup obtained by the method in Example A-5 in an amount of 7%, on dry solid basis, while changing the pH in the saline. Thereafter the eluate was subjected to membrane filtration and sterilely bottled in vials to obtain a liquid agent which contained $10^5$ units/ml of natural human interferon-gamma.

The liquid agent is favorably usable in the treatment of viral diseases, allergic diseases, rheumatism, diabetes and malignant tumors where the liquid agent is perorally or parenterally administered at a dose of 1–20 ml/day/adult. The liquid agent retains its initial activity even when allowed to stand at 4° C. or 25° C. for 20 days because the maltosyl maltoside acts as stabilizer.

EXAMPLE B-17

Liquid tumor necrosis factor agent

A natural human tumor necrosis factor-alpha preparation produced by Hayashibara Biochemical Laboratories, Inc., Okayama, Japan and commercialized by Cosmo Bio Co., Ltd., Tokyo, Japan was applied in usual manner to an immobilized anti-human tumor necrosis factor-alpha antibody column to adsorb thereon the natural human tumor necrosis factor-alpha in the preparation but to pass the calf serum albumin as stabilizer through the column for removal, and the adsorbed human tumor necrosis factor-alpha was eluted by using a physiological saline containing a high-purity maltotriosyl maltoside syrup obtained by the method in Example A-5 in an amount of 10%, on dry solid basis, while changing the pH in the saline. The resultant eluate was subjected to membrane filtration and sterilely bottled in vials to obtain a liquid agent which contained $10^4$ units/ml of natural human tumor necrosis factor-alpha.

The liquid agent is favorably usable in the treatment of viral diseases, allergic diseases, rheumatism, diabetes and malignant tumors where the liquid agent is perorally or parenterally administered at a dose of 1–20 ml/day/adult. The agent retains its initial activity even when allowed to stand at 4° C. or 25° C. for 20 days because the maltotriosyl maltoside acts as stabilizer.

EXAMPLE B-18

Interferon tablet

A natural human interferon-alpha preparation produced by Hayashibara Biochemical Laboratories, Inc., Okayama, Japan and commercialized by Cosmo Bio Co., Ltd., Tokyo, Japan was applied in usual manner to an immobilized anti-human interferon-alpha antibody column to adsorb thereon the natural human interferon-alpha in the preparation but to pass the calf serum albumin as stabilizer through the column for removal, and the adsorbed natural human interferon-alpha was eluted by using a physiological saline containing a high-purity maltotriosyl maltoside powder obtained by the method in Experiment B-1 in an amount of 5%, on dry solid basis, while changing the pH in the saline. The resultant eluate was subjected to membrane filtration, dehydrated and pulverized by the addition of about 20-fold amount of a crystalline anhydrous maltose powder, commercialized by Hayashibara Shoji Co., Ltd., Okayama, Japan under the Registered Trademark of "Finetose T", and the resultant powder was fed to tabletting machine to obtain tablets, about 200 g each, which contained about 150 units/tablet of natural human interferon-alpha.

The tablet is favorably usable as lozenge in the treatment of viral diseases, allergic diseases, rheumatism, diabetes and malignant tumors where the tablet is perorally administered at a dose of about 1–10 tablets/day/adult. In particular, the tablet is favorably usable as therapeutic agent for AIDS patients which have been rapidly increasing in recent years.

The tablet retains its initial activity over an extended time period even when allowed to stand at room temperature because the maltotriosyl maltoside and maltose added as stabilizer function well.

EXAMPLE B-19

Fertilizer rod

A fertilizer composition, N=14%, $P_2O_5$=8%, $K_2O$=12%, pullulan, a powder containing maltosyl maltoside, maltotriosyl maltoside and maltotriosyl maltotrioside obtained by the method in Example A-3, calcium sulfate and water in respective amounts of 70:5:5:15:5 by weight were mixed to homogeneity and the resultant mixture was fed to extruder, L/D=20, compression ratio=1.8, inner diameter of 30 mm for dice, and extruded into short rods while heating at 80° C.

The product has a superior handleability and requires no packaging. The product is rigid enough to use it in whole layer application and the exudation rates of the ingredients are controllable by changing the composition. The product can be incorporated with plant hormones, agricultural medicines and soil conditioners, if necessary.

As evident from the above description, the alpha-D-oligoglucosyl alpha-D-oligoglucoside of this invention is a non-reducing oligosaccharide which is very stable and readily soluble in water, as well as having a superior quality and reduced sweetness. Further the alpha-D-oligoglucosyl alpha-D-oligoglucoside of this invention has an elevated chemical stability and properties of stabilizing amino acids and oligopeptides which readily cause browning reaction, as well as of stabilizing biologically-active substances whose activity or active ingredient readily inactivates. Still further the alpha-D-oligoglucosyl alpha-D-oligoglucoside of this invention has additional features such as activating property, appropriate viscosity and reduced fermentability, as well as having properties of controlling osmotic pressure, imparting gloss, retaining moisture, preventing crystallization of other saccharides and preventing retrogradation of amylaceous substances. These features are all favorably utilizable in the production of various compositions including foods, beverages, cosmetics, pharmaceuticals and shaped bodies. These would make a great contribution in the art.

Thus establishment of non-reducing oligosaccharides including alpha-D-oligoglucosyl alpha-D-oligoglucoside of this invention and its production and use would have an industrial significance in the fields of foods, beverages, cosmetics and pharmaceuticals.

We claim:

1. A non-reducing oligosaccharide which is alpha-D-oligoglucosyl alpha-D-oligoglucoside represented by the formula of "Gm-T-Gn" where "G" and "T" mean a glucose residue and an alpha, alpha-trehalose residue, respectively, which glucose residues are linked to each other and to the trehalose residue via alpha-1,4 or alpha-1,6 linkages, and each of "m" and "n" is an integer of 1–8.

2. The non-reducing oligosaccharide of claim 1, which is a member selected from the group consisting of alpha-D-maltosyl alpha-D-maltoside, alpha-D-maltotriosyl alpha-D-maltoside, and alpha-D-maltotriosyl alpha-D-maltotrioside.

3. The non-reducing oligosaccharide of claim 2, wherein said alpha-D-maltotriosyl alpha-D-maltotrioside is in a crystalline form.

4. The non-reducing oligosaccharide of claim 3, which gives diffraction angles (2 theta) of 7.8°, 10.0, 13.1, 17.5 and 18.2 which exhibit a higher level of strength than other diffraction angles in FIG. 6 on powder x-ray diffraction analysis.

5. A process for producing the non-reducing oligosaccharide of claim 1, said process comprising:

contacting either an aqueous solution which contains trehalose and an alpha-glucosyl saccharide, or an aqueous solution which contains a non-reducing saccharide having a trehalose structure at its end and having a degree of glucose polymerization of at least 3, with a saccharide-transferring enzyme, or successively with a saccharide-transferring enzyme and a hydrolase, to form said non-reducing oligosaccharide; and collecting the non-reducing oligosaccharide.

6. The process of claim 5, wherein said non-reducing oligosaccharide has been formed by contacting a reducing partial starch hydrolysate with an enzyme which produces a non-reducing saccharide.

7. The process of claim 5, wherein said saccharide-transferring enzyme is cyclomaltodextrin glucanotransferase, alpha-amylase or alpha-glucosidase.

8. The process of claim 5, wherein said hydrolase is either beta-amylase or combination of beta-amylase and starch-debranching enzyme.

9. The process of claim 5, wherein said non-reducing saccharide is alpha-D-maltosyl alpha-D-maltoside, alpha-D-maltotriosyl alpha-D-maltoside, or alpha-D-maltotriosyl alpha-D-maltotrioside.

10. A process for producing the non-reducing saccharide of claim 1, said process comprising:

applying a saccharide mixture solution which contains said non-reducing oligosaccharide along with other saccharide(s) to either a strongly-acidic cation exchange resin or octadecyl silica gel to effect chromatography; and collecting a fraction which is rich in said non-reducing oligosaccharide.

11. The process of claim 10, wherein said non-reducing saccharide oligosaccharide is alpha-D-maltosyl alpha-D-maltoside, alpha-D-maltotriosyl alpha-D-maltoside, or alpha-D-maltotriosyl alpha-D-maltotrioside.

12. A composition which comprises the non-reducing oligosaccharide of claim 1 and a carrier selected from the group consisting of foods, beverages, and cosmetics.

13. The composition of claim 12, wherein the amount of said non-reducing oligosaccharide is about 0.1 w/w % or more.

14. The composition of claim 12, wherein said non-reducing oligosaccharide is alpha-D-maltosyl alpha-D-maltoside, alpha-D-maltotriosyl alpha-D-maltoside, or alpha-D-maltotriosyl alpha-D-maltotriosyl alpha-D-maltotrioside.

15. The composition of claim 12, which is for food, beverages, cosmetics or a shaped body.

* * * * *